United States Patent [19]

Atkinson et al.

[11] Patent Number: 5,188,830
[45] Date of Patent: Feb. 23, 1993

[54] METHODS FOR THROMBOLYTIC THERAPY

[75] Inventors: Joseph G. Atkinson, Montreal, Canada; David A. Claremon, Audubon, Pa.; John J. Baldwin, Gwynedd Valley, Pa.; Paul A. Friedman, Rosemont, Pa.; David C. Remy, North Wales, Pa.; Andrew M. Stern, Gwynedd Valley, Pa.

[73] Assignee: Merck & Co., Inc., Rahway, N.J.

[21] Appl. No.: 517,915

[22] Filed: Apr. 2, 1990

Related U.S. Application Data

[62] Division of Ser. No. 32,123, Mar. 27, 1987, abandoned.

[51] Int. Cl.$^5$ .................. A61K 37/547; A61K 37/54; A61K 31/41
[52] U.S. Cl. .................. 424/94.63; 424/94.64; 514/234.5; 514/233.8; 514/321; 514/322; 514/367; 514/375; 514/394; 548/309.7; 548/310.1
[58] Field of Search ............ 514/367, 375, 394, 234.5, 514/233.8, 321, 322; 424/94.64, 3; 548/335

[56] References Cited

U.S. PATENT DOCUMENTS

| | | | |
|---|---|---|---|
| 4,873,346 | 10/1989 | Anderson | 548/157 |
| 4,968,494 | 11/1990 | Claremon et al. | 424/94.63 |
| 5,098,707 | 3/1992 | Baldwin et al. | 424/94.64 |

OTHER PUBLICATIONS

Abdel-Rahman et al., Chem. Abstracts, vol. 107:39674a (1987).
Simonov et al., Chem. Abstracts, vol. 81:25601g (1974).
Miura et al., Chem. Abstracts, vol. 92:32016a (1980).
Barreiro et al., Chem. Abstracts, vol. 98:198085w (1983).
Popov et al., Chem. Abstracts, vol. 74:76369a (1971).

Primary Examiner—Jacqueline Stone
Attorney, Agent, or Firm—Alice O. Robertson; Raymond M. Speer

[57] ABSTRACT

Certain Factor XIIIa inhibitor compounds have been discovered which have been found to be useful in the lysis of blood clots and thus adaptable for administration in thrombolytic therapy either alone or together with plasminogen activator.

14 Claims, 3 Drawing Sheets

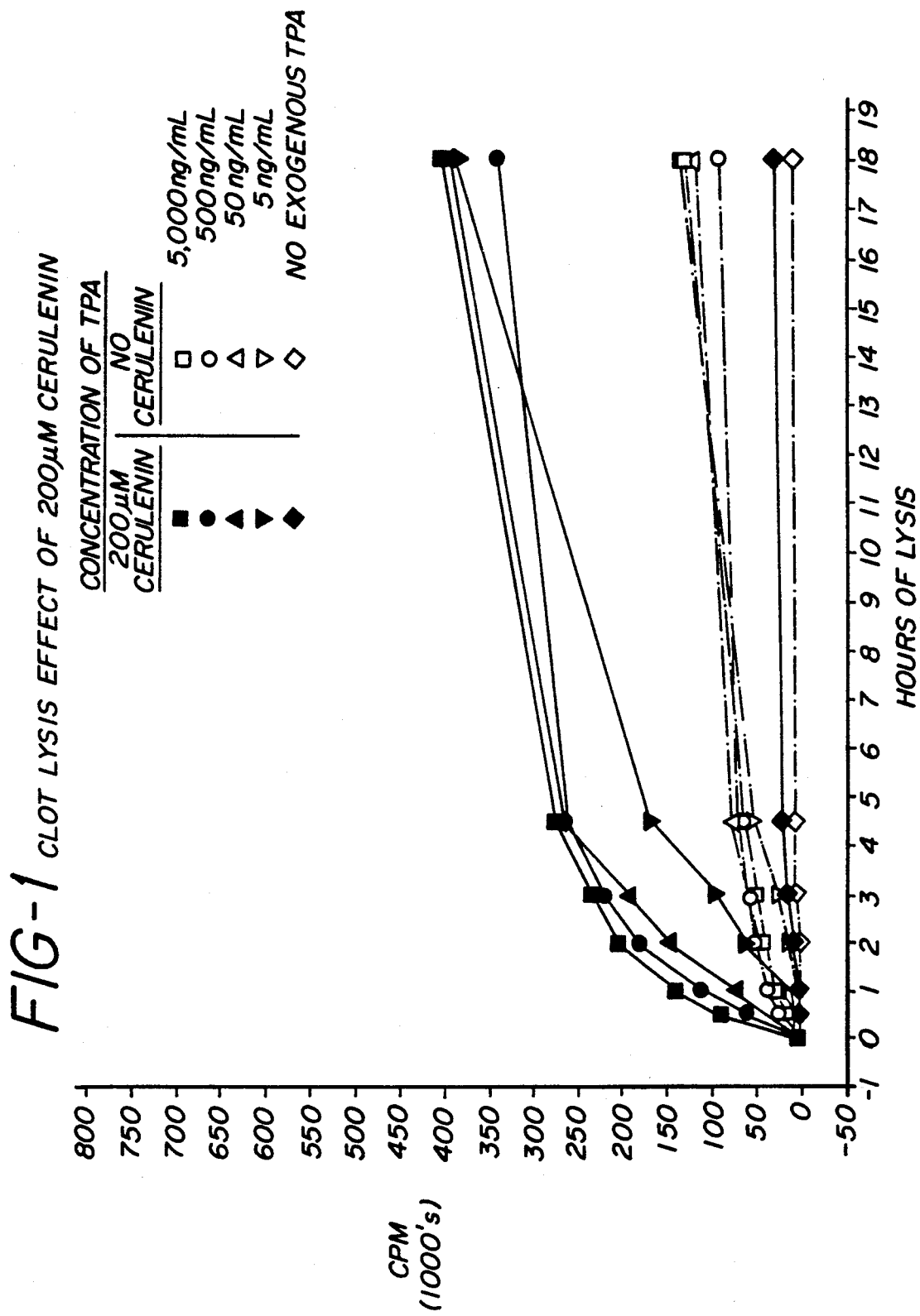

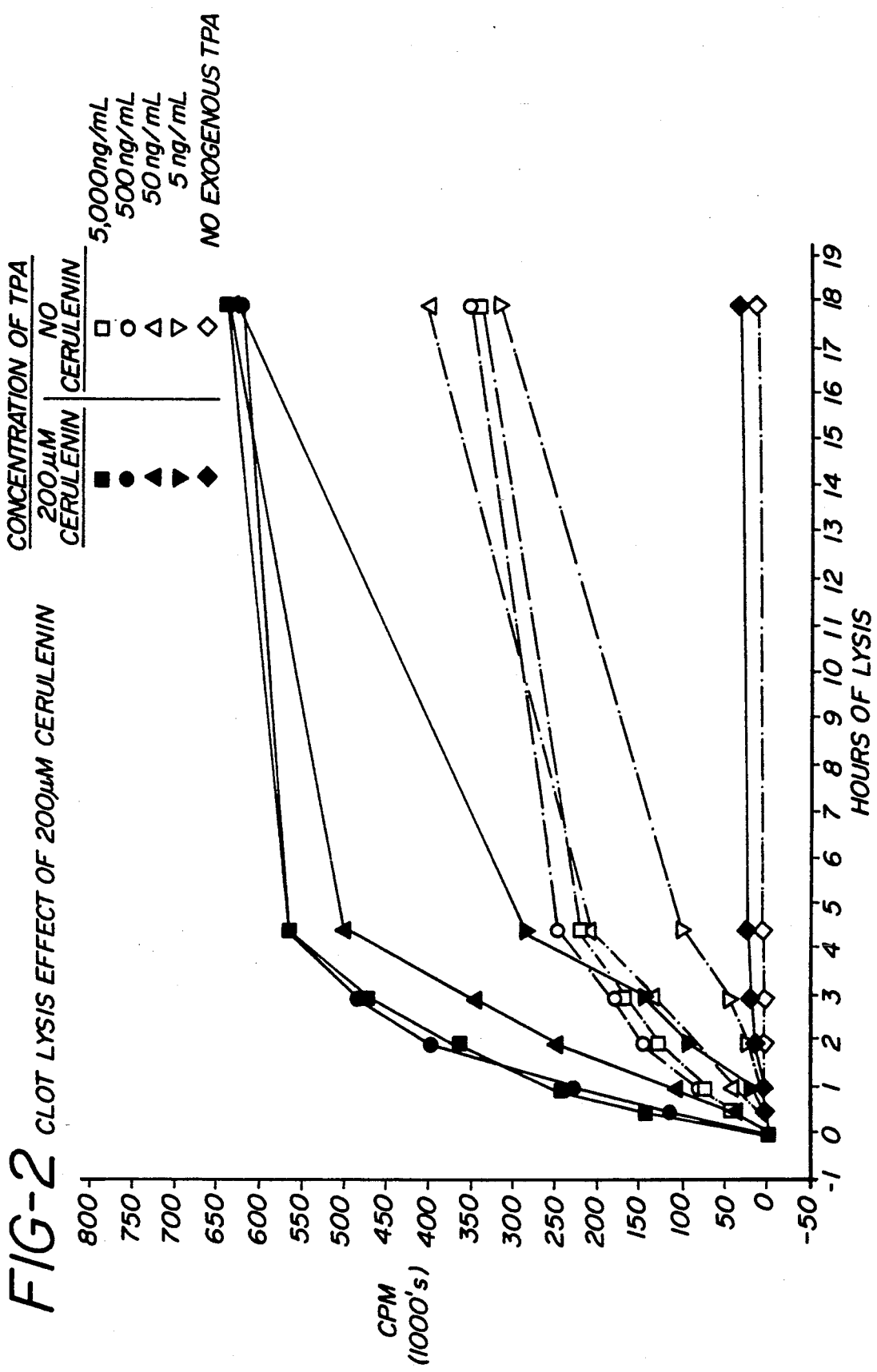

FIG-3 CLOT LYSIS EFFECT OF 20µM THIAZOLIUM PERCHLORATE COMPOUND (TPC)

| CONCENTRATION OF TPA | | |
|---|---|---|
| 20µM TPC | NO TPC | |
| ■ | □ | 5,000 ng/mL |
| ● | ○ | 500 ng/mL |
| ▲ | △ | 50 ng/mL |
| ▶ | ▷ | 5 ng/mL |
| ◆ | ◇ | NO EXOGENOUS TPA |

METHODS FOR THROMBOLYTIC THERAPY

This is a division of application Ser. No. 07/032,123, filed Mar. 27, 1987, abandoned.

BACKGROUND OF THE INVENTION

Thrombosis, an excessive formation of clot within a blood vessel, gives rise to thrombotic strokes, deep vein thrombosis, myocardial infarction and other medical conditions which may result in necrosis of tissues and oftentimes death of a patient. Even if death does not occur, thrombotic attacks are accompanied by damage to cells to which circulation has been prevented by thrombi formation. Removal of the thrombi by lysis is essential and the rate of lysis may be critical in ultimate patient recovery.

Lysis may occur normally in hours or days by the action of a proteolytic enzyme, plasmin, which is present in plasma as the inactive precursor, plasminogen, and which is activated by plasminogen activators, such as (pro)urokinase, urokinase or tissue plasminogen activator. Since the occurrence of a thrombotic event calls for rapid remedial action, administration of exogenous tissue plasminogen activator or (pro)urokinase is currently looked to in thrombolytic or fibrinolytic therapy. However, a still further reduction in lysis time is necessary to minimize cell injury.

Factor XIIIa is an enzyme responsible for the final event in the coagulation of blood. It is a plasma or platelet transglutaminase which is the activated form of Factor XIII, also known as fibrin-stabilizing-factor. It is essential for normal hemostasis and is responsible for the cross-linking of fibrin. This step is sometimes described as the transformation of soft clot to hard clot.

STATEMENT OF THE INVENTION

According to the present invention it has been discovered that by administering a compound hereinafter defined which is a Factor XIIIa inhibitor, blood clots may be more rapidly lysed. Further, it has been discovered that when administered together with tissue plasminogen activator, the time and extent of lysis is increased multifold in vitro. Thus, the discovery has provided a method for thrombolytic or fibrinolytic therapy which comprises administering a therapeutically effective amount of a Factor XIIIa inhibitor compound, alone or in admixture with a tissue plasminogen activator or a combination of plasminogen activators.

DETAILED DESCRIPTION OF THE INVENTION

The present invention is based on the discovery that certain compounds which have been found to inhibit the action of Factor XIIIa, a plasma transglutaminase enzyme which catalyzes a number of reactions stabilizing blood clots, have been found unexpectedly to have the property of making blood clots more susceptible to being lysed either at physiological levels or administered levels of plasminogen activator. It has further been discovered that when a Factor XIIIa inhibitor is employed together with a plasminogen activator, such as tissue plasminogen activator an enzyme which converts plasminogen to plasmin, a multifold increase in the rate and extent of lysis may be achieved. Thus, there is provided a method useful in fibrinolytic therapy which comprises administering a Factor XIIIa inhibitor to a patient suffering from thrombosis or susceptible to thrombotic attack. The method may be employed in acute therapy for immediate and rapid lysis of clots by administering a Factor XIIIa inhibitor together with plasminogen activator to a patient suffering from a thrombotic attack. It is also useful for continued therapy after initial relief from thrombotic attack has been achieved by providing a more complete lysis of the clot and thereby minimizing complications from reocclusion. The method also may be useful as a prophylactic means by administering a Factor XIIIa inhibitor alone to a patient considered to be in a high risk thrombosis category.

One class of Factor XIIIa inhibitor useful in the practice of the present invention is an acyloxiranecarboxylic acid compound represented by the formula

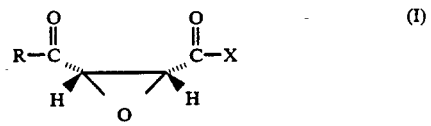

and pharmaceutically acceptable salts. In this and subsequent formulas

R is alkyl, alkenyl or aralkyl;

X is —NHR' or OR" wherein R' and R" independently are hydrogen or lower alkyl.

As employed in the specification and claims, the expressions for the groups have significances hereinafter detailed.

By the expression "alkyl" is meant from 1 to about 10 carbon atoms. By "lower alkyl" is meant from 1 to 5 carbon atoms.

By "alkenyl" is meant an alphatic chain of 2 to about 10 carbon atoms with at least one and up to three double bonds.

By "aralkyl" is meant benzyl or phenylethyl, optionally substituted with alkyl, halo, or lower alkoxy. "Halo" embraces chloro, bromo, fluoro and iodo.

The salts contemplated are primarily sodium and potassium.

The compounds useful in the present invention must be of the cis configuration with respect to the epoxide ring as indicated in Formula I.

The compounds which are amides, i.e., X is —NHR' may be represented as

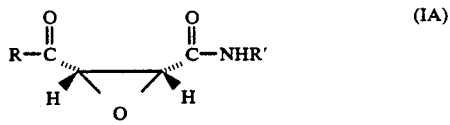

The compounds which are acids or esters, i.e., X is —OR" may be represented as

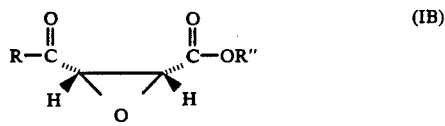

The preferred acyloxiranecarboxylic acid compounds in the practice of the present invention are compounds which are amides, represented by Formula IA. An especially preferred compound is an antibiotic known as cerulenin having antifungal properties and represented by the formula

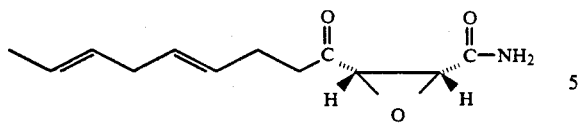

The compound is also known by the chemical name 3-(1-oxo-4,7-nonadienyl)-oxiranecarboxamide or (2R,3S)-2,3-epoxy-4-oxo-7E,10E-dodecadienamide.

The acyloxiranecarboxylic acid compounds to be employed in the present invention may be crystalline solids or high boiling liquids. They are generally of low solubility in water, but of high solubility in solvents such as dimethyl sulfoxide (DMSO), dimethylformamide (DMF) and most common organic solvents.

Another Factor XIIIa inhibitor useful in the practice of the present invention is a heteroarylacrylic acid compound represented by the formula

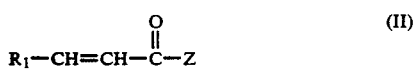

and its pharmaceutically acceptable salts.

In this and subsequent formulas,

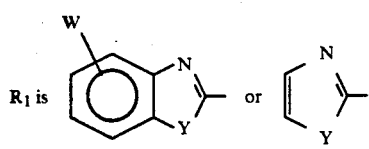

wherein

Y is —NH—, —NR$_2$, —S—, or —O— wherein R$_2$ is lower alkyl;

W is hydrogen lower alkyl, halo, or lower alkoxy; and

Z is —OR$_3$ or —NR$_4$R$_5$ wherein R$_3$ is hydrogen or lower alkyl, and R$_4$ and R$_5$ are independently hydrogen or lower alkyl or together are —(CH$_2$)$_5$— or —(CH$_2$)$_2$—O—(CH$_2$)$_2$—. By "lower alkyl" or "lower alkoxy" as above employed is meant a group having from 1 to 5 carbon atoms.

The compounds which are acids or esters, i.e., Z is —OR$_3$ may be represented by the formulas

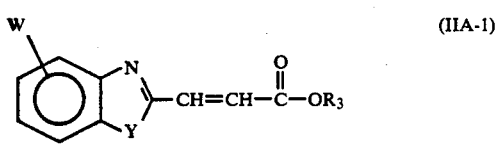

or

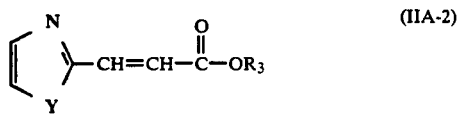

The compounds which are amides, i.e., Z is —NR$_4$R$_5$ may be represented by the formulas

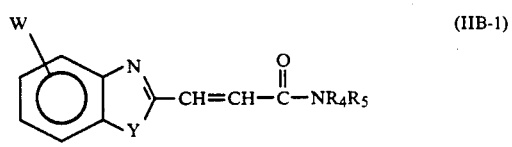

or

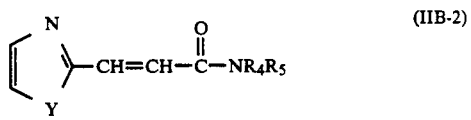

The most preferred heteroarylacrylic acid compound is 3-(benzimidazol-2-yl)acrylic acid represented by the formula

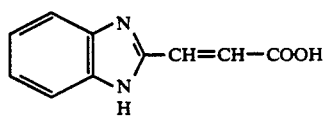

The heteroarylacrylic acid compounds are also generally crystalline solids or high boiling liquids of low solubility in water but soluble in organic solvents.

A compound which has been found to be especially useful is 2-(1-acetonylthio)-5-methylthiazolo(2,3-b)-1,3,4-thiadiazolium perchlorate ("thiadiazolium perchlorate compound") which may be represented by the following formula:

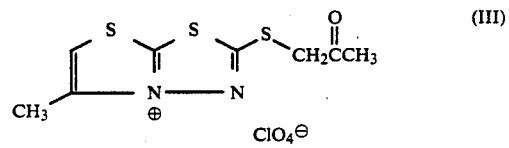

Compounds useful in the fibrinolytic or thrombolytic therapy of the present invention are not limited to those of the foregoing structural classes. Suitable compounds may be identified initially by the Factor XIIIa inhibitor assay hereinafter described. Compounds which would be suitable in thrombolytic therapy generally exhibit at least 50 percent inhibition at a concentration of $1 \times 10^{-5}$M.

The plasminogen activator compounds suitable in the practice of the present invention include tissue plasminogen activator, prourokinase (single chain urokinase), urokinase (dual chain urokinase), streptokinase and eminase (FDC Reports, Sept. 22, 1986, T&G, page 4) as the more important plasminogen activators. The plasminogen activators may be those isolated from natural sources or produced by recombinant technology and include the genetically engineered variants thereof.

The acyloxiranecarboxylic acid compounds (Formula I) may be prepared by a sequence of reactions hereinafter described. Cerulenin itself may be obtained by fermentation according to Japan patent 21,638 (C.A. 73, 108271k (1970)) or by any of the chemical syntheses described in the literature. A recent synthesis by T. Ohta et al., is found in Heterocycles, 24, 1137 (1986).

The acyloxiranecarboxylic acid compounds useful in the present invention may be synthesized by the following sequence of reactions:

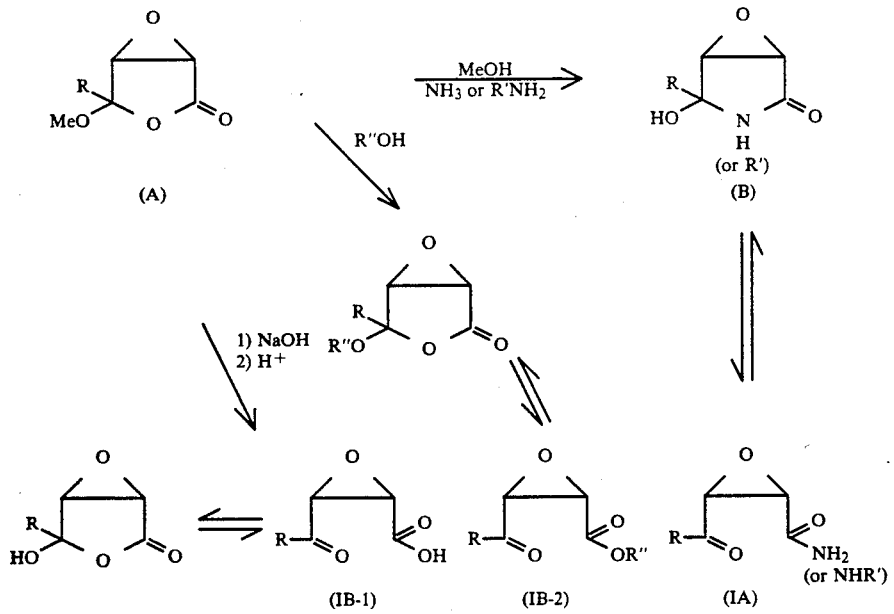

The epoxylactone (A) is transformed into the compounds of Formula I by treatment with the appropriate nitrogen base (ammonia or amine) or the appropriate hydroxy compound (water or alcohol) to obtain the desired amide, ester or acid.

When the desired compound is an amide, the epoxylactone is treated with excess alcoholic ammonia or amine, preferably methanolic ammonia or amine. After completion of the reaction, unreacted ammonia or amine, and solvent are removed by evaporation and the product recovered as residue. The product recovered generally is the cyclic form which may be converted to the open form represented by Formula IA by passing the product through a silica gel column.

In carrying out the reaction, a methanol solution of the epoxylactone (A) is added to a solution of about 16 percent ammonia or amine in methanol at about 0° C. After completion of the addition, the mixture is stirred at 0° C. for about 1.5 hours and then the ammonia or amine and solvent are evaporated to obtain a residue. The latter is chromatographed on silica gel using 10 percent diethyl ether in methylene chloride to obtain compound of Formula IA.

The compounds which are esters, i.e., X is —OR", may be prepared by the reaction of the epoxylactone (A) with an appropriate alcohol (R"OH).

In carrying out the reaction, the epoxylactone is stirred with excess alcohol R"OH for about one hour, and the excess alcohol vaporized off at reduced pressure to obtain the ester product (Formula IB-2) as residue. The latter may be purified by chromatographing on silica gel using methylene chloride/hexane or ethyl acetate/hexane as eluting agent.

The compounds which are acids, i.e., X is OH, may be prepared by treating the epoxylactone with alkali to obtain an alkali salt of the acid which is thereafter carefully acidified to obtain the acid (Formula IB-1).

The starting epoxylactone may be prepared from furfuryl alcohol employing methods similar to that described by above cited Ohta et al for the preparation of cerulenin, which reference is incorporated herein by reference. Briefly, furfuryl alcohol is lithiated with an appropriate lithiating agent such as n-butyl lithium. The lithiated furfuryl alcohol is then reacted with the appropriate RI compound, i.e., an alkyl, alkenyl or aralkyl iodide to obtain 5-R-furfuryl alcohol. The

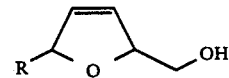

5-R-furfuryl alcohol is then oxidized to a 6-hydroxy-6-R-2H-pyran-3-one, a hemiketal. This may be carried out conveniently by a Sharpless oxidation using for example, vanadyl acetylacetonate and tert-butylhydroperoxide. The 6-hydroxy-6-R-2H-pyran-3-one is then oxidized to a lactol, 4-hydroxy-4-R-2-buten-4-olide. Periodic acid is suitable for this step. The lactol then may be reacted with trimethyl orthoformate and tin (IV) chloride to obtain a

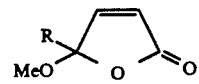

methoxybutenolide which is epoxidized to the starting epoxylactone with sodium hypochlorite in dimethylformamide or a mixture of it with ether. In carrying out each of the steps, conditions similar to that detailed in the preparation of cerulenin may be employed with appropriate modifications or substitutions as desired and within the knowledge of the skilled in the art.

The heteroarylacrylic acid compounds (Formula II) useful in the present invention are readily obtained from the corresponding known heteroarylpropanoic acids as starting materials by oxidation or dehydrogenation, or from heteroaryl-3-hydroxypropanoic acids by dehydration

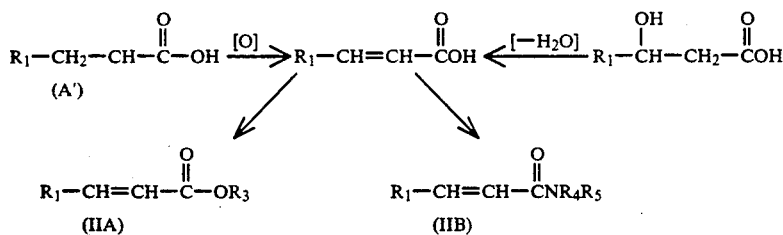

to obtain the appropriate acrylic acid from which esters and amides are made employing conventional procedures.

When the heteroarylacrylic acid is obtained from the heteroarylpropanoic acid by chemical oxidation, suitable oxidizing agents include mercuric acetate, mercuric oxide, potassium permanganate, manganese dioxide, copper oxide, copper sulfate, hydrogen peroxide, ferric chloride, ferric sulfate and the like. Slight excess of the oxidizing agent generally is employed and the reaction is carried out in an organic solvent appropriate for the particular oxidizing agent employed and within the knowledge of the one skilled in the art.

In a representative preparation using mercuric acetate as oxidizing agent, a solution of the appropriate heteroarylalkanoic acid in glacial acetic acid is heated with a solution of mercuric acetate in glacial acetic acid for several hours. At the end of this period, the product may be recovered by first removing glacial acetic acid under reduced pressure, then dissolving the residue in acid, precipitating the mercury with hydrogen sulfide, filtering off the mercuric sulfide and recovering the product from the filtrate by successive appropriate treatments with organic solvent and water.

When the heteroarylacrylic acid is obtained from heteroarylpropanoic acid by dehydrogenation, the reaction may be carried out in the presence of suitable catalysts such as nickel, copper, platinum and palladium using conditions appropriate for the particular catalyst. However, chemical methods of oxidation are preferred.

When the desired acrylic acid compound is to be obtained by the dehydration of heteroaryl-3-hydroxypropanoic acid, it may be carried out simply by heating the hydroxypropanoic acid compound under reduced pressure and elevated temperatures. Temperatures in the range of 150°-200° C. at 3 to 4 mm. pressure are satisfactory.

In carrying out the reaction, unmodified heteroaryl-3-hydroxypropanoic acid is heated in an appropriate vessel for such time as necessary for completion of the dehydration as seen by the cessation in the completion of the evolution of water vapor. The resulting acrylic acid compound may be recovered by dissolving in dilute sodium carbonate and then reprecipitating with hydrochloric acid.

The esters (Formulas IIA-1 and IIA-2) may be prepared from the acid by preparing the acid chloride with thionyl chloride and then reacting the acid chloride with the appropriate $R_3OH$. If a methyl ester, it may be prepared directly from methanol in the presence of hydrogen chloride.

The amides (Formulas IIB-1 and IIB-2) may be prepared from the acid by preparing the acid chloride with thionyl chloride and then reacting the acid chloride with the appropriate amine. The reaction may be carried out in an inert solvent such as toluene, benzene and the like.

2-(1-Acetonylthio)-5-methylthiazolo(2,3-b)-1,3,4-thiadiazolium perchlorate is a crystalline solid which may be prepared in accordance with the following sequence of reactions:

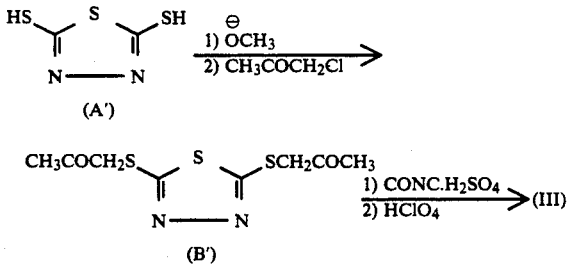

The preparation and properties of the compound is fully described in a Ph.D. thesis entitled "Thiazolo[2,3-b]thiazolium and Analogous Cations" by William Jonas Jones, Jr. submitted to Duke University and which is incorporated by reference.

Briefly, 1,3,4-thiadiazole-2,5-dithiol (A') is added to absolute methanol containing sodium metal. Chloroacetone is then added and the resulting mixture stirred together to obtain the bis(acetonylthio) compound (B') as a precipitate. The latter is recovered and then heated with concentrated sulfuric acid at about 100° C. and thereafter the mixture treated with perchloric acid and cooled to 0° C. to obtain the desired thiadiazolium perchlorate compound (III).

The usefulness of the Factor XIIIa inhibitors for enhancing the rate of clot lysis catalyzed by plasminogen activators may be demonstrated first by establishing the inhibitory potencies of the compounds in a Factor XIIIa assay. Then a subsequent assay is used to determine the rate of clot lysis.

The Factor XIIIa inhibitor assay is based on the incorporation of $^{14}C$-putrescine into casein catalyzed by Factor XIIIa. The assay is carried out employing the procedure described in Methods in Enzymology, Vol. 45, Ch 15., pages 177–191 (1976) and using Factor XIII (F XIII) isolated from human plasma. The procedure is summarized briefly and schematically illustrated as follows:

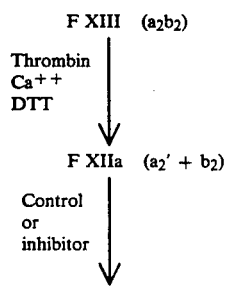

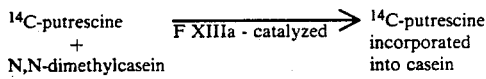

Factor XIII assay mixtures are prepared by adding stepwise, appropriate prepared solutions of thrombin and dithiothreitol (DTT) to a mixture comprising Factor XIII in glycerol/water and tris(hydroxymethyl)aminomethane hydrochloride (Tris.HCl). To a portion of the mixture is added calcium chloride as source of calcium ions required for enzyme activity and to the remaining mixture is added instead of calcium ions ethylenediaminetetraacetic acid (EDTA) which serves as a blank for background.

A substrate mixture is prepared from $^{14}C$-putrescine and N,N-dimethylcasein.

The assay tubes and control tubes are charged with the substrate mixture and incubated at 37° C. for 20 minutes. Samples are withdrawn from each tube, spotted onto a filter disk which is then immersed in ice cold trichloroacetic acid solution to precipitate the casein on the filter. The filter is then washed to remove unincorporated or free $^{14}C$-putrescine and after drying is counted for $^{14}C$-putrescine incorporated to casein from which percent activity and/or inhibition can be calculated.

The results with cerulenin, 3-(benzimidazol-2-yl)acrylic and the thiadiazolium perchlorate compound were as follows:

| Inhibitor Concentration | Percent Inhibition |
|---|---|
| 3-(Benzimidazol-2-yl)-acrylic acid | |
| $1.3 \times 10^{-5}M$ | 91 |
| $4.5 \times 10^{-6}M$ | 78 |
| $1.5 \times 10^{-6}M$ | 52 |
| $5 \times 10^{-7}M$ | 19 |
| $1.7 \times 10^{-7}M$ | 9 |
| Cerulenin | |
| $6.2 \times 10^{-5}M$ | 100 |
| $6.2 \times 10^{-6}M$ | 64 |
| $6.2 \times 10^{-7}M$ | 22 |
| Thiadiazolium perchlorate compound | |
| $1.4 \times 10^{-5}M$ | 100 |
| $5 \times 10^{-6}M$ | 100 |
| $1.6 \times 10^{-6}M$ | 99 |
| $5 \times 10^{-7}M$ | 84 |
| $2 \times 10^{-7}M$ | 24 |
| $6 \times 10^{-8}M$ | 9 |

The usefulness of Factor XIIIa inhibitor compounds in lysing clots and/or inhibiting clot formation may be demonstrated in an in vitro clot lysis assay.

In the assay, whole blood or plasma is charged with $^{125}I$-fibrinogen. Thrombin is added to initiate clot formation and subsequently incubated for 2 hours to complete the cross-linking by endogenous Factor XIII. Factor XIIIa inhibitor is added prior to clot initiation or at various times during the 2-hour incubation. At the end of this period, the labelled clot is washed and lysis is initiated by exogenous tissue plasminogen activator (TPA). Exogenous plasminogen is employed in some experiments. Endogenous plasminogen is used for others. Clot dissolution as a function of time is monitored by the release of solubilized $^{125}I$-fibrin-derived fragments.

In one set of experiments with no exogenous plasminogen, TPA was employed as the plasminogen activator at different levels with and without 200 μM cerulenin as the factor XIIIa inhibitor. The results seen in FIG. 1 show that there are enhanced rates and extents of lysis in the presence of cerulenin at both physiological and pharamcological levels of TPA.

In another set of experiments, 12 μg/mL of exogenous glu-plasminogen (glutamic plasminogen) was employed to enhance the rate and extent of TPA catalyzed clot lysis. Under these conditions in the presence of 200 μM cerulenin, lysis rates were further enhanced in a relative similar way as seen in FIG. 2.

In still another set of experiments with no exogenous plasminogen, TPA was employed as the plasminogen activator at different levels with and without the thiazolium perchlorate compound as the factor XIIIa inhibitor compound. The results seen in FIG. 3 show that there are enhanced rates and extents of lysis in the presence of the thiazolium perchlorate compound at both physiological and pharmacological levels of TPA.

In FIGS. 1 and 2, the open symbols indicate absence of cerulenin and the closed symbols indicate the presence of 200 μM cerulenin at the time of clot formation. Clot lysis is conducted in buffer, pH 7.5; 5 ng/mL TPA represents approximate physiologic concentration. 50 to 5,000 mg/mL represents pharmacologic concentration range. FIG. 1 studies did not employ exogenous glu-plasminogen. FIG. 2 studies employed glu-plasminogen levels at approximately 10 percent physiologic level (12 μ/mL).

The process of the present invention for enhancing clot lysis and/or for inhibiting clot formation comprises intravenously administering a therapeutic dose of a Factor XIIIa inhibitor compound in a composition comprising the same. In general, the dose may be that sufficient to provide between about 2 micrograms per kilogram of body weight per day to about 100 milligrams/kilogram/day while considering patient's health, weight, age and other factors which influence drug response. The drug may be administered either by a single injection, multiple injections or continuous infusion.

In the preferred process of the present invention, Factor XIIIa inhibitor compound is administered with a plasminogen activator in a combination therapy. When Factor XIIIa inhibitor compound and plasminogen activator are employed in a combination therapy, it is most desirable to use plasminogen activator in the dose range of 5 to 40,000 I.U./kg/hr and Factor XIIIa inhibitor compound in the range of 10 μg–10 mg/kg/hour.

When combination therapy is employed, it is preferable to administer the Factor XIIIa inhibitor compound first in a single bolus and thereafter to administer the plasminogen activator by continuous infusion. Alternatively, it may be administered simultaneously as a continuous infusate. Under certain circumstances it may be desirable to administer subsequent to the administration of the plasminogen activator. However, it is intended that the method of the present invention embrace concurrent administration as well as sequential administration in any order.

When the Factor XIIIa inhibitor compound is employed alone, particularly for a prophylactic purpose, it may be employed in the range of from 10 μg to 100 mg/kg/day and administered either orally or parenterally.

Compositions to be employed in the practice of the present invention comprises a Factor XIIIa inhibitor compound in sterile physiologically acceptable media such as physiological saline. Such compositions may also contain other ingredients for purposes such as for aiding solubility or for preservation or the like, said ingredients being acceptable for intravenous administration. The compositions may be prepared as concentrate compositions which may be appropriately diluted to the appropriate treating composition immediately prior to administration. A therapeutic composition as a unitary dose form may contain from 2 μg to 1000 mg of Factor XIIIa inhibitor compound and as concentrate composition may contain up to 10 grams of the compound. Compositions suitable in the preferred practice of the present invention of co-administering plasminogen activator and Factor XIIIa inhibitor compound may contain from 50,000 to 2 million I.U. of TPA and from 100 mg to 7 grams of Factor XIIIa inhibitor compound.

The preferred compositions are those in which the Factor XIIIa is cerulenin, 2-(1-acetonylthio)-5-methylthiazolo(2,3-b)-1,3,4-thiadiazolium perchlorate or 3-(benzimidazol-2-yl)acrylic acid.

Parenteral compositions may be prepared employing the foregoing preferred compounds or one of the following compounds as active ingredient in a manner hereinafter described. These compositions are merely illustrative and are not to be construed as limiting.

3-(1-oxo-7-nonaenyl)oxiranecarboxamide
3-(1-oxo-nonanyl)oxiranecarboxamide
3-(1-oxo-6-phenylpropyl)oxiranecarboxamide
N-Methyl-3-(1-oxo-4,7-nonadienyl)oxiranecarboxamide
n-Propyl 3-(1-oxo-4,7-nonadienyl)oxirancecarboxylate
3-(5-methylbenzimidazol-2-yl)acrylic acid
3-(5-isopropoxybenzimidazol-2-yl)acrylic acid
3-(5-chlorobenzimidazol-2-yl)acrylic acid
3-(Imidazol-2-yl)acrylic acid
3-(Oxazol-2-yl)acrylic acid
3-(Thiazol-2-yl)acrylic acid
3-(Benzoxazol-2-yl)acrylic acid
3-(Benzthiazol-2-yl)acrylic acid

PARENTERAL COMPOSITION

One liter of a parenteral composition comprising one of the preferred compounds or one of the foregoing compounds may be prepared from the following formulation:

|  | Grams |
|---|---|
| Active Ingredient | 5.0 |
| Polysorbate 80 | 2.0 |
| Sodium Chloride | 9.0 |
| Sodium carboxymethyl cellulose | 10.0 |
| Methyl paraben | 1.8 |
| Propyl paraben | 0.2 |
| Water, USP q.s. to 1 liter |  |

The parabens, sodium chloride and carboxymethylcellulose are dissolved in one-half the total volume of water by heating to 95° C. to obtain a solution which is then filtered and autoclaved. The polysorbate is dissolved in one-third of the total volume of water, and the resulting solution also filtered and autoclaved. Sterile active ingredient is added to the second solution and the mixture passed through a sterile colloid mill to obtain a suspension of active ingredient. The first solution is added to the suspension with stirring then U.S.P. water added to 1 liter. Sterile vials are filled with the suspension while stirring.

Oral compositions also may be prepared from one of the above-named compounds as active ingredient in admixture with a pharmaceutically acceptable carrier. Suitable carriers include for liquid compositions include water, glycols, oils, alcohols, flavoring agents, preservatives, coloring agents and the like; for solid preparations, starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed.

A representative composition is the following:

ORAL COMPOSITION 5000 compressed tablets, each containing as active ingredient 100 milligrams of active ingredient are prepared from the following formulation:

|  | Grams |
|---|---|
| Active Ingredient | 500 |
| Starch | 700 |
| Dibasic calcium phosphate hydrous | 5000 |
| Calcium stearate | 25 |

The ingredients are finely powdered, mixed well, and then granulated with 10 percent starch paste. The granulation is dried and compressed into tablets using starch as a disintegrant and calcium stearate as lubricant.

What is claimed is:

1. A method for lysing clots in thrombotic patients which comprises intravenously administering a therapeutically effective amount of a composition comprising a Factor XIIIa inhibitor compound, said Factor XIIIa inhibitor compound being a heteroarylacrylic acid compound represented by the formula

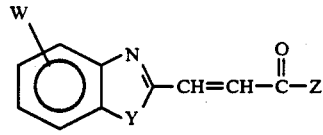

and its pharmaceutically acceptable salts wherein
Y is —NH, —NR$_2$, —S—, —O—, where R$_2$ is lower alkyl;
W is hydrogen, lower alkyl, halo or lower alkoxy; and
Z is —OR$_3$ or —NR$_4$R$_5$ wherein R$_3$ is hydrogen or lower alkyl and R$_4$ and R$_5$ are independently hydrogen or lower alkyl.

2. A method according to claim 1 wherein in the heteroarylacrylic acid Factor XIIIa inhibitor compound of the formula

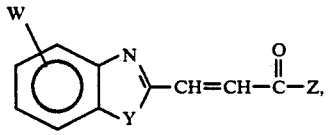

Y is NH or NR$_2$.

3. A method according to claim 2 wherein in the formula of the heteroarylacrylic acid compound, Z is $OR_3$ wherein R is H or lower alkyl.

4. A method according to claim 3 wherein R is H.

5. A method according to claim 4 wherein the compound is 3-(benzimidazol-2-yl)acrylic acid.

6. A method according to claim 1 wherein plasminogen activator is also administered.

7. A method according to claim 6 wherein the plasminogen activator is selected from the group consisting of tissue plasminogen activator, urokinase, prourokinase, streptokinase and eminase.

8. A method according to claim 7 wherein the plasminogen activator is tissue plasminogen activator.

9. A method according to claim 1 wherein from 2 µg/kg/day to 100 mg/kg/day of heteroarylacrylic acid compound is employed.

10. A method according to claim 9 wherein from 5 to 40,000 I.U./kg/hr of plasminogen activator is also administered.

11. A method according to claim 1 wherein the therapeutic dose is delivered by a single, multiple or continuous intravenous administration.

12. A method according to claim 11 wherein the therapeutic dose is delivered by continuous infusion.

13. A method according to claim 12 wherein the Factor XIIIa inhibitor compound is administered first in a single bolus and the plasminogen activator then administered by continuous infusion.

14. A method for lysing clots in thrombotic patients according to claim 11 which comprises co-administering intravenously from 10 µg/kg/hr to 10 mg/kg/hr of heteroarylacrylic acid compound and 5 to 40,000 I.U./kg/hr of tissue plasminogen activator.

* * * * *